(12) United States Patent
Raillard et al.

(10) Patent No.: US 7,989,641 B2
(45) Date of Patent: Aug. 2, 2011

(54) METHODS OF SYNTHESIZING N-HYDROXYSUCCINIMIDYL CARBONATES

(75) Inventors: Stephen P. Raillard, Mountain View, CA (US); Suresh K. Manthati, Sunnyvale, CA (US); Peng Liu, King of Prussia, PA (US); Qunying Dai, King of Prussia, PA (US); Hao Yin, King of Prussia, PA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

(21) Appl. No.: 12/537,764

(22) Filed: Aug. 7, 2009

(65) Prior Publication Data

US 2010/0081830 A1    Apr. 1, 2010

Related U.S. Application Data

(60) Provisional application No. 61/087,038, filed on Aug. 7, 2008, provisional application No. 61/086,821, filed on Aug. 7, 2008.

(51) Int. Cl.
    *C07D 207/00* (2006.01)
(52) U.S. Cl. ..................... 548/542; 560/115
(58) Field of Classification Search .......... 548/542; 560/115
    See application file for complete search history.

(56) References Cited

U.S. PATENT DOCUMENTS

| | | | |
|---|---|---|---|
| 4,126,684 | A | 11/1978 | Robson et al. |
| 4,760,057 | A | 7/1988 | Alexander |
| 4,916,230 | A | 4/1990 | Alexander |
| 5,006,560 | A | 4/1991 | Kreutner et al. |
| 5,684,018 | A | 11/1997 | Alexander |
| 5,719,185 | A | 2/1998 | Bountra et al. |
| 6,117,908 | A | 9/2000 | Andrews et al. |
| 6,818,787 | B2 | 11/2004 | Gallop et al. |
| 6,833,140 | B2* | 12/2004 | Cundy et al. ............. 424/468 |
| 6,927,036 | B2 | 8/2005 | Gallop et al. |
| 6,972,341 | B2 | 12/2005 | Gallop et al. |
| 7,109,239 | B2 | 9/2006 | Gallop et al. |
| 7,186,855 | B2 | 3/2007 | Gallop et al. |
| 7,227,028 | B2 | 6/2007 | Gallop et al. |
| 7,232,924 | B2 | 6/2007 | Raillard et al. |
| 7,300,956 | B2 | 11/2007 | Gallop et al. |
| 7,351,740 | B2 | 4/2008 | Zerangue et al. |
| 2005/0070715 | A1 | 3/2005 | Bhat et al. |
| 2005/0154057 | A1 | 7/2005 | Estrada et al. |
| 2008/0161393 | A1 | 7/2008 | Barrett et al. |
| 2009/0118365 | A1 | 5/2009 | Benson et al. |
| 2009/0192222 | A1 | 7/2009 | Yao et al. |
| 2009/0192325 | A1 | 7/2009 | Gallop et al. |
| 2009/0215809 | A1 | 8/2009 | Yao et al. |

FOREIGN PATENT DOCUMENTS

| | | |
|---|---|---|
| WO | WO 01/05813 A1 | 1/2001 |
| WO | WO 01/08675 A1 | 2/2001 |
| WO | WO 01/26638 A2 | 4/2001 |
| WO | WO 02/096404 A1 | 12/2002 |
| WO | WO 02/100347 A2 | 12/2002 |
| WO | WO 2004/089289 A2 | 10/2004 |
| WO | WO 2005/010011 A2 | 2/2005 |
| WO | WO 2005/027850 A2 | 3/2005 |
| WO | WO 2005/066122 A2 | 7/2005 |
| WO | WO 2008/077241 A1 | 7/2008 |

OTHER PUBLICATIONS

Sun, Xicheng. Synthesis and Evaluation of Novel Pseudomycin Side-Chain Analogues, Part 3. Bioorganic and Medicinal Chemistry Letters. 11 (2001) 3055-3059.*
Kouge et al., Peptide synthesis in aqueous solution. I. Application of p-dialkyl-sulfoniophenols as a water-soluble coupling reagent, *Bull. Chem. Soc. Jpn.* (1987), 60: 2409-2418.
International Search Report, dated Jan. 4, 2010, issued in corresponding PCT application No. PCT/US2009/053188 (5 pages).
Written Opinion of the International Searching Authority, dated Jan. 4, 2010, issued in corresponding PCT application No. PCT/US2009/053188 (5 pages).
U.S. Appl. No. 61/087,056, filed Aug. 7, 2008, Raillard et al.
Ciccaglione et al., Effect of acute and chronic administration of the $GABA_B$ agonist baclofen on 24 hour pH metry and symptoms in control subjects and in patients with gastro-oesophageal reflux disease. *Gut* (2003), 52, 464-470.
Van Herwaarden et al., The effect of baclofen on gastro-oesophageal reflux, lower oesophageal sphincter function and reflux symptoms in patients with reflux disease. *Aliment. Pharmacol. Ther.* (2002), 16, 1655-1662.

* cited by examiner

*Primary Examiner* — Rebecca Anderson
*Assistant Examiner* — Samantha Shterengarts
(74) *Attorney, Agent, or Firm* — Dorsey & Whitney LLP

(57) ABSTRACT

The present disclosure relates to methods of synthesizing N-hydroxysuccinimidyl-carbonate intermediates from the corresponding sulfones useful in the preparation of 1-(acyloxy)-alkyl carbamate prodrugs.

19 Claims, No Drawings

METHODS OF SYNTHESIZING N-HYDROXYSUCCINIMIDYL CARBONATES

This application claims the benefit under 35 U.S.C. §119(e) of U.S. Provisional Application Ser. Nos. 61/087,038 filed Aug. 7, 2008; and 61/086,821 filed Aug. 7, 2008, each of which is incorporated by reference in its entirety.

FIELD

Disclosed herein are methods of synthesizing N-hydroxysuccinimidyl-carbonate intermediates from the corresponding sulfones used in the preparation of 1-(acyloxy)-alkyl carbamate prodrugs.

BACKGROUND

The oral bioavailability of certain drugs can be improved by conversion to prodrugs. Certain prodrugs are derivatives of the parent drug in which a functional group is "masked" by a promoiety. Following administration to a patient the prodrug is metabolized to release the parent drug.

The 1-(acyloxy)-alkyl functionality is an example of a promoiety that has been used to functionalize amino containing drugs such as gabapentin, pregabalin, R-baclofen, and tranexamic acid. Gabapentin ([1-(aminomethyl)cyclohexyl] acetic acid) is an FDA approved drug that is marketed for the treatment of post herpetic neuralgia and epilepsy. 1-{[(α-Isobutanoyloxyethoxy)carbonyl]aminomethyl}-1-cyclohexane acetic acid is a 1-(acyloxy)-alkyl carbamate prodrug of gabapentin that has utility in the treatment of epilepsy (Gallop et al., WO 02100347), pain (Gallop et al., WO 02100347), particularly neuropathic pain or pain associated with irritable bowel syndrome, anxiety (Gallop et al., WO 02100347), particularly general anxiety disorder, alcohol dependency or ethanol withdrawal syndrome (Gallop et al., WO 02100347), restless legs syndrome (Barrett and Canafax, WO 2005027850), migraine prophylaxis (Barrett and Cundy, US 20080161393), fibromyalgia (Barrett and Cundy, US 20080161393), and hot flashes (Barrett and Gallop, WO 2004089289), particularly hot flashes associated with menopause. Pregabalin ((S)-3-(aminomethyl)-5-methyl-hexanoic acid) is an FDA approved drug that is marketed for the treatment of post herpetic neuralgia, fibromyalgia, and epilepsy. Pregabalin is not absorbed from the lower gastrointestinal tract and exhibits a short half life in vivo, and therefore frequent dosing is required to maintain therapeutic levels in the body. (3S)-{[1-Isobutanoyloxyethoxy]carbonylaminomethyl}-5-methyl-hexanoic acid, (3S)-{[1-isobutanoyloxy-isobutoxy]carbonylaminomethyl}-5-methyl-hexanoic acid, and (3S)-{[1-benzoyloxyethoxy]carbonylaminomethyl}-5-methyl-hexanoic acid are examples of 1-(acyloxy)-alkyl carbamate prodrugs of the GABA analog pregabalin, (3S)-aminomethyl-5-methyl-hexanoic acid, which exhibit high bioavailability as pregabalin when dosed either orally or directly into the colon of a mammal (Gallop et al., U.S. Pat. No. 6,972,341 and U.S. Pat. No. 7,186,855; and Yao et al., U.S. application Ser. Nos. 12/358,454 and 12/358,507 filed Jan. 23, 2009). The 1-(acyloxy)-alkyl promoiety has also been used to provide prodrugs of baclofen ((R)-4-amino-3-(4-chlorophenyl)butanoic acid). Gallop et al., U.S. Pat. No. 7,109,239 and U.S. Pat. No. 7,300,956 disclose 1-(acyloxy)-alkyl carbamate prodrugs of R-baclofen such as (3R)-4-{[(1S)-2-methyl-1-(2-methylpropanoyloxy)propoxy]carbonylamino}-3-(4-chlorophenyl)butanoic acid. R-Baclofen is known to be useful for treating spasticity and gastro-esophageal reflux disease (van Herwaarden et al., *Aliment. Pharmacol. Ther.* 2002, 16(9), 1655-62; Ciccaglione and Marzio, *Gut* 2003, 52(4), 464-70; Andrews et al., U.S. Pat. No. 6,117,908; and Fara et al., WO 02096404); in promoting alcohol abstinence in alcoholics (Gessa et al., WO 0126638); in promoting smoking cessation (Gessa et al., WO 0108675); in reducing addiction liability of narcotic agents (Robson et al., U.S. Pat. No. 4,126,684); in the treatment of emesis (Bountra et al., U.S. Pat. No. 5,719,185); as an anti-tussive for the treatment of cough (Kreutner et al., U.S. Pat. No. 5,006,560); as well as for treating neuropathic and musculoskeletal pain (Benson et al., US 20090118365), movement disorders such as dystonia and hiccups; peripheral nerve disorders such as muscle stimulation disorders; spinal cord disorders such as spastic paraparesis; cranial nerve disorders such as glossopharyngeal neuralgia and trigeminal neuralgia; multiple sclerosis; and cerebral palsy.

The 1-(acyloxy)-alkyl promoiety has also been used to provide prodrugs of tranexamic acid (trans-4-(aminomethyl)-cyclohexanecarboxylic acid). For example, Zerangue et al., U.S. Pat. No. 7,351,740, disclose 1-(acyloxy)-alkyl carbamate prodrugs of tranexamic acid such as 4-({[[(2-methylpropanoyloxy)ethoxy]carbonylamino}methyl)cyclohexanecarboxylic acid. Tranexamic acid is known to be useful in treating bleeding such as excessive menstrual bleeding (menorrhagia), bleeding associated with cardiac surgery, upper gastrointestinal hemorrhage, blood loss in patients with advanced cancer, bleeding that occurs during dental procedures in hemophiliacs and skin conditions such as wound healing, epidermal hyperplasia, skin roughening, unwanted skin pigmentation, and tumor metastasis (Zerangue et al., U.S. Pat. No. 7,351,740).

Methods of synthesizing 1-(acyloxy)-alkyl carbamate prodrugs are disclosed in Gallop et al., U.S. Pat. Nos. 6,818,787, 6,927,036, 6,972,341, 7,186,855, and 7,227,028; Raillard et al., U.S. Pat. No. 7,232,924; Gallop and Bhat, WO 2005/01001); and in Alexander, U.S. Pat. Nos. 4,760,057, 4,916,230, and 5,684,018.

Other methods of synthesizing 1-(acyloxy)alkyl carbamate prodrugs are more recently disclosed by Raillard et al., U.S. Provisional Application No. 61/087,056 filed Aug. 7, 2008.

SUMMARY

Methods of synthesizing 1-(acyloxy)-alkyl N-hydroxysuccinimidyl carbonate intermediates employing the conversion of a corresponding sulfone are disclosed.

In a first aspect, methods of synthesizing a 1-(acyloxy) alkyl N-hydroxysuccinimidyl carbonate compound of Formula (I) or a salt thereof are disclosed comprising:

reacting a compound of Formula (V) or a salt thereof with an N-hydroxysuccinimide compound of Formula (VII) to provide the compound of Formula (I):

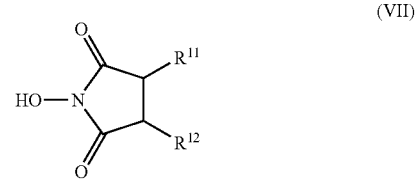

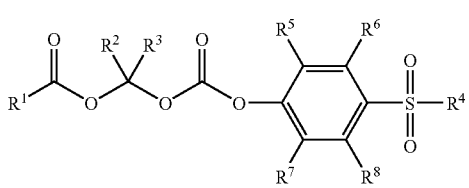

(V)

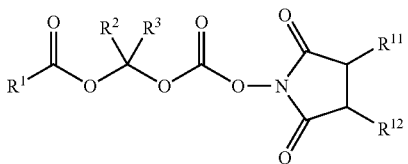

(I)

wherein:
R¹ is chosen from $C_{1-6}$ alkyl, substituted $C_{1-6}$ alkyl, $C_{3-6}$ cycloalkyl, substituted $C_{3-6}$ cycloalkyl, phenyl, substituted phenyl, and $C_{7-9}$ phenylalkyl;

R² and R³ are independently chosen from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, and $C_{7-9}$ phenylalkyl; or R² and R³ together with the carbon atom to which they are bonded form a ring chosen from a cyclobutyl, cyclopentyl, and cyclohexyl ring;

R⁴ is chosen from $C_{1-4}$ alkyl and substituted $C_{1-4}$ alkyl wherein each of the one or more substituent groups is independently chosen from halogen, halo-$C_{1-3}$ alkyl, hydroxyl, and cyano;

each of R⁵, R⁶, R⁷, and R⁸ is independently chosen from hydrogen, halogen, $C_{1-3}$ alkyl, and halo-$C_{1-3}$ alkyl; and R¹¹ and R¹² are independently chosen from hydrogen, $C_{1-16}$ acylamino, $C_{1-16}$ acyloxy, $C_{1-6}$ alkoxycarbonylamino, $C_{1-6}$ alkoxycarbonyloxy, $C_{1-4}$ alkyl, substituted $C_{1-4}$ alkyl, $C_{1-6}$ alkoxy, substituted $C_{1-6}$ alkoxy, $C_{6-12}$ aryl, substituted $C_{6-12}$ aryl, $C_{7-16}$ arylalkyl, $C_{1-6}$ carbamoyl, $C_{1-6}$ dialkylamino, $C_{5-12}$ heteroaryl, hydroxyl, and sulfonamide; or R¹¹ and R¹² together with the atoms to which they are bonded form a ring chosen from a substituted $C_{3-12}$ cycloalkyl, substituted $C_{3-12}$ heterocycloalkyl, and substituted $C_{6-12}$ aryl ring.

In a second aspect, 1-(acyloxy)-alkyl N-hydroxysuccinimidyl carbonate compounds of Formula (I) or a salt thereof prepared by the methods provided by the present disclosure are disclosed.

DETAILED DESCRIPTION

Definitions

A dash ("-") that is not between two letters or symbols is used to indicate a point of attachment for a moiety or substituent. For example, —CONH₂ is bonded through the carbon atom.

"Alkoxy" by itself or as part of another substituent refers to a radical —OR²⁰ where R²⁰ is chosen from alkyl, heteroalkyl, cycloalkyl, heterocycloalkyl, cycloalkylalkyl, heterocycloalkylalkyl, aryl, heteroaryl, arylalkyl, and heteroarylalkyl, as defined herein. Examples of alkoxy groups include, but are not limited to, methoxy, ethoxy, propoxy, butoxy, cyclohexyloxy, and the like. In certain embodiments, an alkoxy group is $C_{1-18}$ alkoxy, in certain embodiments, $C_{1-12}$ alkoxy, in certain embodiments, $C_{1-6}$ alkoxy, in certain embodiments, $C_{1-4}$ alkoxy, and in certain embodiments, $C_{1-3}$ alkoxy.

"Alkyl" by itself or as part of another substituent refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$), in certain embodiments from 1 to 10 carbon atoms ($C_{1-10}$), in certain embodiments from 1 to 8 carbon atoms ($C_{1-8}$), in certain embodiments from 1 to 6 carbon atoms ($C_{1-6}$), in certain embodiments from 1 to 4 carbon atoms ($C_{1-4}$), and in certain embodiments from 1 to 3 carbon atoms ($C_{1-3}$).

"Acyl" by itself or as part of another substituent refers to a radical —C(O)R²¹, wherein R²¹ is chosen from hydrogen, alkyl, cycloalkyl, heterocycloalkyl, aryl, arylalkyl, heteroalkyl, heteroaryl, heteroarylalkyl as defined herein. Examples of acyl groups include formyl, acetyl, cyclohexylcarbonyl, cyclohexylmethylcarbonyl, benzoyl, benzylcarbonyl, and the like.

"Acylamino" by itself or as part of another substituent refers to a radical —N(H)C(O)R²², wherein R²² is chosen from hydrogen, alkyl, cycloalkyl, heterocycloalkyl, aryl, arylalkyl, heteroalkyl, heteroaryl, heteroarylalkyl as defined herein. Examples of acylamino groups include formylamino, acetylamino, cyclohexylcarbonylamino, cyclohexylmethylcarbonylamino, benzoylamino, benzylcarbonylamino, and the like. In certain embodiments, an acylamino group is $C_{1-16}$ acylamino, $C_{1-8}$ acylamino, and in certain embodiments, $C_{1-6}$ acylamino.

"Acyloxy" by itself or as part of another substituent refers to a radical —OC(O)R²³, wherein R²³ is chosen from hydrogen, alkyl, cycloalkyl, heterocycloalkyl, aryl, arylalkyl, heteroalkyl, heteroaryl, heteroarylalkyl as defined herein. In certain embodiments, an acyloxy group is $C_{1-16}$ acyloxy, $C_{1-8}$ acyloxy, $C_{1-4}$ acyloxy, and in certain embodiments $C_{1-3}$ acyloxy.

"Alkoxycarbonyl" by itself or as part of another substituent refers to a radical —C(O)OR²⁴ where R²⁴ represents an alkyl or cycloalkyl group as defined herein. Examples of alkoxycarbonyl groups include methoxycarbonyl, ethoxycarbonyl, propoxycarbonyl, butoxycarbonyl, cyclohexyloxycarbonyl, and the like. In certain embodiments, an alkoxycarbonyl group is $C_{1-8}$ alkoxycarbonyl, $C_{1-6}$ alkoxycarbonyl, $C_{1-4}$ alkoxycarbonyl, and in certain embodiments, $C_{1-3}$ alkoxycarbonyl.

"Alkoxycarbonylamino" by itself or as part of another substituent refers to a radical —N(H)C(O)OR²⁵ where R²⁵ represents an alkyl or cycloalkyl group as defined herein. Examples of alkoxycarbonylamino groups include methoxycarbonylamino, ethoxycarbonylamino, propoxycarbonylamino, butoxycarbonylamino, cyclohexyloxycarbonylamino, and the like. In certain embodiments, an alkoxycarbonylamino group is $C_{1-8}$ alkoxycarbonylamino, $C_{1-6}$ alkoxycarbonylamino, $C_{1-4}$ alkoxycarbonylamino, and in certain embodiments, $C_{1-3}$ alkoxycarbonylamino.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), and in certain embodiments, from 6 to 10 carbon atoms ($C_{6-10}$). Aryl, however, does not encompass or overlap in any way with heteroaryl, separately defined herein.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{6-20}$, in certain embodiments, an arylalkyl group is $C_{6-18}$ arylalkyl, e.g., the alkanyl, alkenyl or alkynyl moiety of the arylalkyl group is $C_{1-8}$ and the aryl moiety is $C_{6-10}$.

"Carbamoyl" by itself or as part of another substituent refers to a radical —OC(O)N(H)$R^{26}$ wherein $R^{26}$ is chosen from alkyl and cycloalkyl as defined herein. In certain embodiments, a carbamoyl group is $C_{1-8}$ carbamoyl, $C_{1-6}$ carbamoyl, $C_{1-4}$ carbamoyl, and in certain embodiments, $C_{1-3}$ carbamoyl.

"Compounds" of the present disclosure include any specific compounds within the formulae disclosed herein. Compounds may be identified either by their chemical structure and/or chemical name. Compounds are named using Chemistry 4-D Draw Pro, version 7.01c (ChemInnovation Software, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to those skilled in the art.

Compounds of the present disclosure such as for example compounds of Formulae (I), (V), (VI), and (VII) include, but are not limited to, optical isomers of the compounds, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column. In addition, compounds of the present disclosure include Z- and E-forms (or cis- and trans-forms) of compounds with double bonds. Compounds of the present disclosure may also exist in several tautomeric forms including the enol form, the keto form, and mixtures thereof. Accordingly, the chemical structures depicted herein encompass all possible tautomeric forms of the illustrated compounds. Compounds of the present disclosure also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated, or N-oxides. When reference is made to compounds of the present disclosure, such as compounds of Formulae (I), (V), (VI), and (VII), it is understood that a compound also implicitly refers to salts, solvates, hydrates, and combinations of any of the foregoing. Certain compounds may exist in multiple crystalline, co-crystalline, or amorphous forms. Compounds of the present disclosure include pharmaceutically acceptable salts thereof, or pharmaceutically acceptable solvates of the free acid form of any of the foregoing, as well as crystalline forms of any of the foregoing.

Further, when partial structures of the compounds are illustrated, an asterisk (*) indicates the point of attachment of the partial structure to the rest of the molecule.

"Cycloalkyl" by itself or as part of another substituent refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-8}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{4-30}$ cycloalkylalkyl, e.g., the alkanyl, alkenyl, or alkynyl moiety of the cycloalkylalkyl group is $C_{1-10}$ and the cycloalkyl moiety is $C_{3-20}$, and in certain embodiments, a cycloalkylalkyl group is $C_{3-20}$ cycloalkylalkyl, e.g., the alkanyl, alkenyl, or alkynyl moiety of the cycloalkylalkyl group is $C_{1-8}$ and the cycloalkyl moiety is $C_{3-12}$.

"Dialkylamino" by itself or as part of another substituent refers to a radical —$N(R^{27})_2$, wherein each $R^{27}$ is independently alkyl as defined herein. $C_{1-6}$ dialkylamino means that each $R^{27}$ is independently $C_{1-6}$ alkyl. In certain embodiments, a dialkylamino group is $C_{1-8}$ dialkylamino, $C_{1-6}$ dialkylamino, $C_{1-4}$ dialkylamino, and in certain embodiments, $C_{1-3}$ dialkylamino.

"Drug" as defined under 21 U.S.C. §321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . ." In certain embodiments, a drug is a primary or secondary amine containing drug having the structure $HNR^9R^{10}$, where $R^9$ is hydrogen or a bond to $R^{10}$, and $R^{10}$ is the drug without the primary amine group —$NH_2$ or secondary amine group —NH—. For a primary amine containing drug $R^9$ is hydrogen and the drug has the structure $H_2N$—$R^{10}$, and for a secondary amine containing drug $R^{10}$ is a bond and the drug has the structure HN—(—$R^{10}$). Examples of primary amine containing drugs include, for example, gabapentin, pregabalin, R-baclofen, and tranexamic acid. Examples of secondary amine containing drugs include, for example, meropenem, salmeterol, benzapril, ramipril, ciprofloxacin, and fenoldopam. Examples of drugs containing both primary and secondary amine groups include, for example, cisapride, amifostine, and gentamycin.

"GABA analog" refers to a compound having the structure:

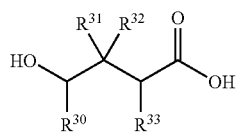

wherein:
$R^{30}$ and $R^{33}$ are independently chosen from hydrogen, $C_{1-6}$ alkyl, substituted $C_{1-6}$ alkyl, $C_{6-10}$ aryl, substituted $C_{6-10}$ aryl, $C_{7-16}$ arylalkyl, substituted $C_{7-16}$ arylalkyl, $C_{3-10}$ cycloalkyl, and substituted $C_{3-10}$ cycloalkyl;
$R^{31}$ and $R^{32}$ are independently chosen from hydrogen, $C_{1-6}$ alkyl, substituted $C_{1-6}$ alkyl, $C_{6-10}$ aryl, substituted $C_{6-10}$ aryl, $C_{7-16}$ arylalkyl, substituted $C_{7-16}$ arylalkyl, $C_{3-10}$ cycloalkyl, and substituted $C_{3-10}$ cycloalkyl; or $R^{31}$ and $R^{32}$ together with the carbon atom to which they are bonded form a $C_{3-10}$ cycloalkyl, substituted $C_{3-10}$ cycloalkyl, $C_{3-10}$ heterocycloalkyl, or substituted $C_{3-10}$ heterocyloalkyl ring.

In certain embodiments of a GABA analog, each substituent group is independently chosen from halogen, —$NH_2$, —OH, —CN, —COOH, —$C(O)NH_2$, —$C(O)OR^{40}$, and —$NR^{40}_3{}^+$ wherein each $R^{40}$ is independently $C_{1-3}$ alkyl.

In certain embodiments of a GABA analog, each of $R^{30}$ and $R^{33}$ is hydrogen. In certain embodiments of a GABA analog, $R^{31}$ is chosen from $C_{1-4}$ alkyl, substituted $C_{1-4}$ alkyl, $C_{1-4}$ alkoxycarbonyl, $C_{3-5}$ cycloalkyl, $C_{3-6}$ cycloalkoxycarbonyl, phenyl, substituted phenyl, and $C_{7-9}$ phenylalkyl; and $R^{32}$ is hydrogen. In certain embodiments of a GABA analog, each of $R^{30}$ and $R^{33}$ is hydrogen; $R^{31}$ is chosen from $C_{1-4}$ alkyl, substituted $C_{1-4}$ alkyl, $C_{1-4}$ alkoxycarbonyl, $C_{3-5}$ cycloalkyl, $C_{3-6}$ cycloalkoxycarbonyl, phenyl, substituted phenyl, and $C_{7-9}$ phenylalkyl; and $R^{32}$ is hydrogen.

In certain embodiments of a GABA analog, each of $R^{30}$, $R^{31}$, and $R^{32}$ is hydrogen; and $R^{33}$ is chosen from isobutyl and 4-chlorophenyl.

In certain embodiments, a GABA analog is chosen from gabapentin, pregabalin, and R-baclofen. In certain embodiments, a GABA analog is gabapentin, in certain embodiments, R-baclofen, and in certain embodiments, pregabalin.

"Halogen" refers to a fluoro, chloro, bromo, or iodo group. In certain embodiments, halogen refers to a chloro group.

"Halo-alkyl" refers to an alkyl group as defined herein in which at least one hydrogen atom has been replaced with a halogen. Examples of halo-alkyl groups include fluoroethyl, trifluoromethyl, and trifluoroethyl.

"Heteroalkyl" by itself or as part of another substituent refer to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —$NR^{28}$, =N—N=, —N=N—, —N=N—$NR^{28}$, —$PR^{28}$—, —$P(O)_2$—, —$POR^{28}$—, —O—$P(O)_2$—, —SO—, —$SO_2$—, —$Sn(R^{28})_2$—, and the like, where each $R^{28}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{5-12}$ heteroaryl, substituted $C_{5-12}$ heteroaryl, $C_{7-18}$ heteroarylalkyl, or substituted $C_{7-18}$ heteroarylalkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example $C_{1-6}$ heteroalkyl includes groups having five carbon atoms and one heteroatom, groups having four carbon atoms and two heteroatoms, etc. In certain embodiments, each $R^{28}$ is independently chosen from hydrogen and $C_{1-3}$ alkyl. In certain embodiments, a heteroatomic group is chosen from —O—, —S—, —NH—, —$N(CH_3)$—, and —$SO_2$—. In certain embodiments, a heteroatomic group is chosen from —O— and —NH—.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. In certain embodiments, when the total number of N, S, and O atoms in the heteroaryl group exceeds one, the heteroatoms are not adjacent to one another. In certain embodiments, the total number of heteroatoms in the heteroaryl group is not more than two.

Examples of heteroaryl groups include, but are not limited to, groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. In certain embodiments, a heteroaryl group is from 4- to 20-membered heteroaryl ($C_{4-20}$), and in certain embodiments from 4- to 12-membered heteroaryl ($C_{4-10}$). In certain embodiments, heteroaryl groups are those derived from thiophene, pyrrole, benzothiophene, benzofuran, indole, pyridine, quinoline, imidazole, oxazole, or pyrazine. For example, in certain embodiments, $C_5$ heteroaryl can be furyl, thienyl, pyrrolyl, imidazolyl, pyrazolyl, isothiazolyl, isoxazolyl. In certain embodiments, a heteroaryl group is $C_{5-12}$ heteroaryl, $C_{5-8}$ heteroaryl, $C_{5-6}$ heteroaryl, $C_6$ heteroaryl, and in certain embodiments, $C_5$ heteroaryl.

"Heteroarylalkyl" by itself or as part of another substituent refers to an acyclic alkyl radical in which one of the hydrogen atoms bonded to a carbon atom, is replaced with a heteroaryl group. Typically a terminal or $sp^3$ carbon atom is the atom replaced with the heteroaryl group. In certain embodiments, a heteroarylalkyl group is a 6- to 30-membered heteroarylalkyl ($C_{6-30}$), e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl. In certain embodiments, a heteroarylalkyl group is $C_{7-18}$ heteroarylalkyl, $C_{7-12}$ heteroarylalkyl, $C_{7-10}$ heteroarylalkyl, and in certain embodiments, $C_{7-8}$ heteroarylalkyl.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system no longer contains at least one aromatic ring. Examples of heteroatoms to replace the carbon atom(s) include, but are not limited to, N, P, O, S, Si, etc. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like. In certain embodiments, a heteroatom is chosen from O and N. In certain embodiments, a heterocycloalkyl group is $C_{3-12}$ heterocycloalkyl, $C_{3-10}$ heterocycloalkyl, $C_{3-8}$ heterocycloalkyl, $C_{3-7}$ heterocycloalkyl, and in certain embodiments, $C_{3-6}$ heterocycloalkyl.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of out-of-plane π-electrons corresponding to the Hückel rule (4n+2). Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, pharmaceutically acceptable addition salts include metal salts such as sodium, potassium, aluminum, calcium, magnesium and zinc salts, and ammonium salts such as isopropylamine, diethylamine, and diethanolamine salts. In certain embodiments, a pharmaceutically acceptable salt is the hydrochloride salt. In certain embodiments, a pharmaceutically acceptable salt is the sodium salt. Pharmaceutically acceptable salts may be prepared by the skilled chemist, by treating, for example, a compound of Formula (VI) with an appropriate base in a suitable solvent, followed by crystallization and filtration.

"Prodrug" refers to a derivative of an active compound (drug) that undergoes a transformation under the conditions of use, such as within the body, to release an active drug. Prodrugs are frequently, but not necessarily, pharmacologically inactive until converted into the active drug. Prodrugs can be obtained by bonding a promoiety (defined herein), typically via a functional group, to a drug. For example, R-baclofen prodrug (1) is metabolized within a patient's body to form the parent drug R-baclofen.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Salt" refers to a chemical compound consisting of an assembly of cations and anions. Salts of a compound of the present disclosure include stoichiometric and non-stoichiometric forms of the salt. In certain embodiments, because of the potential use in medicine, salts of a compound of Formula (VI) are pharmaceutically acceptable salts.

"Solvate" refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The term "hydrate" refers to a solvate in which the one or more solvent molecules is water. In certain embodiments, compounds of the present disclosure and salts thereof may form solvates.

"Substituted" refers to a group in which one or more hydrogen atoms are independently replaced with the same or different substituent group(s). In certain embodiments, each s substituent group is independently chosen from halogen, —OH, —CN, —CF$_3$, =O, —NO$_2$, C$_{1-3}$ alkoxy, C$_{1-3}$ alkyl, —COOR$^{13}$ wherein R$^{13}$ is chosen from hydrogen and C$_{1-3}$ alkyl, and —NR$^{13}$$_2$ wherein each R$^{13}$ is independently chosen from hydrogen and C$_{1-3}$ alkyl. In certain embodiments, each substituent group is independently chosen from halogen, —OH, —CN, —CF$_3$, —OCF$_3$, =O, —NO$_2$, C$_{1-6}$ alkoxy, C$_{1-6}$ alkyl, —COOR$^{13}$, —NR$^{13}$$_2$, and —CONR$^{13}$$_2$; wherein each R$^{13}$ is independently chosen from hydrogen and C$_{1-6}$ alkyl. In certain embodiments, each substituent group is independently chosen from —OH, —NH$_2$, and C$_{1-3}$ alkyl.

Reference is now made in detail to certain embodiments of compounds, compositions, and methods. The disclosed embodiments are not intended to be limiting of the claims. To the contrary, the claims are intended to cover all alternatives, modifications, and equivalents.

Methods of Synthesis

Methods provided by the present disclosure include methods of synthesizing a 1-(acyloxy)alkyl N-hydroxysuccinimidyl carbonate compound of Formula (I) or a salt thereof comprising:
reacting a compound of Formula (V) or a salt thereof with an N-hydroxysuccinimide compound of Formula (VII) or a salt thereof to provide the corresponding compound of Formula (I) or a salt thereof:

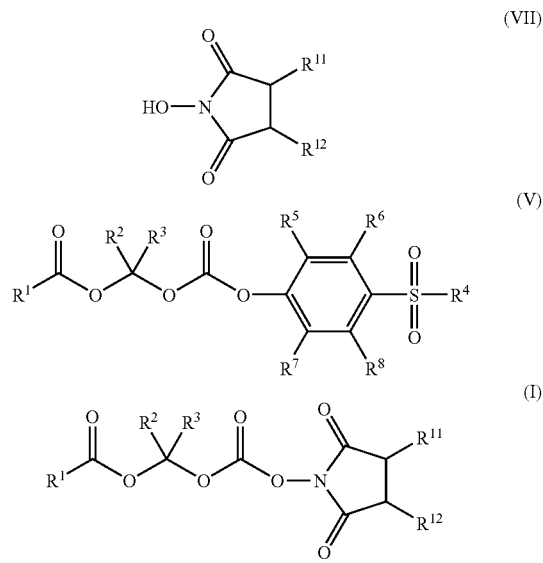

wherein:
R$^1$ is chosen from C$_{1-6}$ alkyl, substituted C$_{1-6}$ alkyl, C$_{3-6}$ cycloalkyl, substituted C$_{3-6}$ cycloalkyl, phenyl, substituted phenyl, and C$_{7-9}$ phenylalkyl;
R$^2$ and R$^3$ are independently chosen from hydrogen, C$_{1-4}$ alkyl, substituted C$_{1-4}$ alkyl, C$_{1-4}$ alkoxycarbonyl, C$_{3-6}$ cycloalkyl, C$_{3-6}$ cycloalkoxycarbonyl, phenyl, substituted phenyl, and C$_{7-9}$ phenylalkyl; or R$^2$ and R$^3$ together with the carbon atom to which they are bonded form a ring chosen from a cyclobutyl, cyclopentyl, and cyclohexyl ring;
R$^4$ is chosen from C$_{1-4}$ alkyl and substituted C$_{1-4}$ alkyl wherein each of the one or more substituent groups is independently chosen from halogen, halo-C$_{1-3}$ alkyl, hydroxyl, and cyano;
each of R$^5$, R$^6$, R$^7$, and R$^8$ is independently chosen from hydrogen, halogen, C$_{1-3}$ alkyl, and halo-C$_{1-3}$ alkyl; and
R$^{11}$ and R$^{12}$ are independently chosen from hydrogen, C$_{1-16}$ acylamino, C$_{1-16}$ acyloxy, C$_{1-6}$ alkoxycarbonylamino, C$_{1-6}$ alkoxycarbonyloxy, C$_{1-4}$ alkyl, substituted C$_{1-4}$ alkyl, C$_{1-6}$ alkoxy, substituted C$_{1-6}$ alkoxy, C$_{6-12}$ aryl, substituted C$_{6-12}$ aryl, C$_{7-16}$ arylalkyl, C$_{1-6}$ carbamoyl, C$_{1-6}$ dialkylamino, C$_{5-12}$ heteroaryl, hydroxyl, and sulfonamide; or R$^{11}$ and R$^{12}$ together with the atoms to which they are bonded form a ring chosen from a substituted C$_{3-12}$ cycloalkyl, substituted C$_{3-12}$ heterocycloalkyl, and substituted C$_{6-12}$ aryl ring.

In certain embodiments, methods provided by the present disclosure comprise:
reacting the compound of Formula (I) or a salt thereof with a primary or secondary amine-containing drug of the formula $HNR^9R^{10}$ or a salt thereof to provide a corresponding 1-(acyloxy)-alkyl carbamate compound of Formula (VI):

$$\underset{R^1}{\overset{O}{\|}}-O-\underset{R^2}{\overset{R^3}{|}}-O-\underset{\underset{R^{10}}{|}}{\overset{O}{\|}}-N-R^9 \quad (VI)$$

In certain embodiments of compounds of Formula (I), Formula (V), and Formula (VI), $R^1$ is chosen from methyl, ethyl, n-propyl, isopropyl n-butyl, isobutyl, sec-butyl, tert-butyl, n-pentyl, isopentyl, sec-pentyl, neopentyl, 1,1,diethoxyethyl, phenyl, and cyclohexyl.

In certain embodiments of compounds of Formula (I), Formula (V), and Formula (VI), one of $R^2$ and $R^3$ is hydrogen and the other of $R^2$ and $R^3$ is chosen from hydrogen, methyl, ethyl, n-propyl, isopropyl, n-butyl, isobutyl, sec-butyl, phenyl, and cyclohexyl.

In certain embodiments of compounds of Formula (I), Formula (V), and Formula (VI), $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; one of $R^2$ and $R^3$ is hydrogen, and the other of $R^2$ and $R^3$ is chosen from methyl, ethyl, n-propyl, and isopropyl.

In certain embodiments of compounds of Formula (I), Formula (V), and Formula (VI), $R^2$ is chosen from methyl, methoxycarbonyl, ethoxycarbonyl, isopropoxycarbonyl, and cyclohexyloxycarbonyl; and $R^3$ is methyl.

In certain embodiments of compounds of Formula (I), Formula (V), and Formula (VI), $R^2$ and $R^3$ together with the carbon atom to which they are bonded form a ring chosen from a cyclobutyl, cyclopentyl, and cyclohexyl ring.

In certain embodiments of compounds of Formula (I), Formula (V), and Formula (VI), $R^1$ is isopropyl; $R^2$ is methyl; and $R^3$ is hydrogen.

In certain embodiments of compounds of Formula (I), Formula (V), and Formula (VI), $R^1$ is isopropyl; $R^2$ is isopropyl; and $R^3$ is hydrogen.

In certain embodiments of compounds of Formula (I), Formula (V), and Formula (VI), $R^2$ and $R^3$ are different, such that the carbon atom to which $R^2$ and $R^3$ are bonded is a stereogenic center.

In certain embodiments of compounds of Formula (I), Formula (V), and Formula (VI), $R^1$ is isopropyl; $R^2$ is isopropyl; $R^3$ is hydrogen; and the stereochemistry at the carbon to which $R^2$ and $R^3$ are bonded is of the S-configuration.

In certain embodiments of compounds of Formula (I), Formula (V), and Formula (VI), $R^1$ is isopropyl; $R^2$ is isopropyl; $R^3$ is hydrogen; and the stereochemistry at the carbon to which $R^2$ and $R^3$ are bonded is of the R-configuration.

In certain embodiments of compounds of Formula (I), Formula (V), and Formula (VI), $R^1$ is isopropyl; $R^2$ is methyl; $R^3$ is hydrogen; and the stereochemistry at the carbon to which $R^2$ and $R^3$ are bonded is of the R-configuration.

In certain embodiments of compounds of Formula (I), Formula (V), and Formula (VI), $R^1$ is isopropyl; $R^2$ is methyl; $R^3$ is hydrogen; and the stereochemistry at the carbon to which $R^2$ and $R^3$ are bonded is of the S-configuration.

In certain embodiments of compounds of Formula (V), $R^4$ is chosen from $C_{1-4}$ alkyl, phenyl, and $C_{5-6}$ cycloalkyl.

In certain embodiments of compounds of Formula (V), $R^4$ is $C_{1-4}$ alkyl.

In certain embodiments of compounds of Formula (V), $R^4$ is methyl.

In certain embodiments of compounds of Formula (V), each of $R^5$, $R^6$, $R^7$, and $R^8$ is hydrogen.

In certain embodiments of compounds of Formula (I) and Formula (VII), each of $R^{11}$ and $R^{12}$ is hydrogen.

In certain embodiments of compounds of Formula (I) and Formula (VII), $R^{11}$ and $R^{12}$ are independently chosen from $C_{1-16}$ acyloxy, substituted $C_{1-16}$ alkoxy, $C_{1-6}$ alkoxycarbonyloxy, $C_{1-6}$ alkoxy, $C_{1-6}$ carbamoyl, and hydroxy.

In certain embodiments of compounds of Formula (I) and Formula (VII), $R^{11}$ and $R^{12}$ are independently chosen from acetoxy, isobutyroyloxy, pivaloyloxy, benzoyloxy, $C_{1-4}$ alkyl-substituted benzoyloxy, methoxy, and benzyloxy.

In certain embodiments of compounds of Formula (I) and Formula (VII), $R^{11}$ and $R^{12}$ are the same and are chosen from isobutyroyloxy and benzoyloxy. In certain embodiments of compounds of Formula (I) and Formula (VII), $R^{11}$ and $R^{12}$ are the same and are isobutyroyloxy and in certain embodiments, are benzoyloxy.

In certain embodiments of compounds of Formula (I), $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; one of $R^2$ and $R^3$ is hydrogen, and the other of $R^2$ and $R^3$ is chosen from methyl, ethyl, n-propyl, and isopropyl; and $R^{11}$ and $R^{12}$ are independently chosen from $C_{1-16}$ acyloxy, substituted $C_{1-16}$ alkoxy, $C_{1-6}$ alkoxycarbonyloxy, $C_{1-6}$ alkoxy, $C_{1-6}$ carbamoyl, and hydroxy. In certain embodiments of compounds of Formula (I), $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; one of $R^2$ and $R^3$ is hydrogen, and the other of $R^2$ and $R^3$ is chosen from methyl, ethyl, n-propyl, and isopropyl; and $R^{11}$ and $R^{12}$ are independently chosen from acetoxy, isobutyroyloxy, pivaloyloxy, benzoyloxy, $C_{1-4}$ alkyl-substituted benzoyloxy, methoxy, and benzyloxy. In certain embodiments of compounds of Formula (I), $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; one of $R^2$ and $R^3$ is hydrogen, and the other of $R^2$ and $R^3$ is chosen from methyl, ethyl, n-propyl, and isopropyl; and $R^{11}$ and $R^{12}$ are the same and are chosen from isobutyroyloxy and benzoyloxy. In certain embodiments of compounds of Formula (I), $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; one of $R^2$ and $R^3$ is hydrogen, and the other of $R^2$ and $R^3$ is chosen from methyl, ethyl, n-propyl, and isopropyl; each of $R^{11}$ and $R^{12}$ are hydrogen.

In certain embodiments of compounds of Formula (V), $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; one of $R^2$ and $R^3$ is hydrogen, and the other of $R^2$ and $R^3$ is chosen from methyl, ethyl, n-propyl, and isopropyl; $R^4$ is chosen from $C_{1-4}$ alkyl, phenyl, and $C_{5-6}$ cycloalkyl; and each of $R^5$, $R^6$, $R^7$, and $R^8$ is hydrogen. In certain embodiments of compounds of Formula (V), $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; one of $R^2$ and $R^3$ is hydrogen, and the other of $R^2$ and $R^3$ is chosen from methyl, ethyl, n-propyl, and isopropyl; $R^4$ is $C_{1-4}$ alkyl; and each of $R^5$, $R^6$, $R^7$, and $R^8$ is hydrogen. In certain embodiments of compounds of Formula (V), $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; one of $R^2$ and $R^3$ is hydrogen, and the other of $R^2$ and $R^3$ is chosen from methyl, ethyl, n-propyl, and isopropyl; $R^4$ is methyl; and each of $R^5$, $R^6$, $R^7$, and $R^8$ is hydrogen.

In certain methods provided by the present disclosure, one of $R^2$ and $R^3$ is hydrogen; and the other of $R^2$ and $R^3$ is chosen from hydrogen, methyl, ethyl, n-propyl, isopropyl, n-butyl, isobutyl, sec-butyl, phenyl, and cyclohexyl; $R^4$ is chosen from $C_{1-4}$ alkyl, phenyl, and $C_{5-6}$ cycloalkyl; each of $R^5$, $R^6$, $R^7$, and $R^8$ is hydrogen; and $R^{11}$ and $R^{12}$ are the same and are chosen from hydrogen, isobutyroyloxy, and benzoyloxy.

In certain embodiments, methods provided by the present disclosure are used for the preparation of 1-({[α-isobutanoyloxyethoxy}carbonyl]aminomethyl)-1-cyclohexane acetic acid, (3R)-4-{[(1S)-2-methyl-1-(2-methylpropanoyloxy)propoxy]carbonylamino}-3-(4-chlorophenyl) butanoic acid; 1-(R)-3-({[1-(2-methylpropanoyloxy)ethoxy] carbonylamino}methyl) (3S)-5-methylhexanoic acid; (+)-trans-4-({[(1S)-1-(2-methylpropanoyloxy)ethoxy] carbonylamino}methyl)-cyclohexanecarboxylic acid; (−)-trans-4-({[(1R)-1-(2-methylpropanoyloxy)ethoxy] carbonylamino}methyl)-cyclohexanecarboxylic acid, or a salt of any of the foregoing.

In certain embodiments, methods provided by the present disclosure are used for the preparation of 1-(acyloxy)-alkyl carbamate prodrugs of R-baclofen of Formula (I):

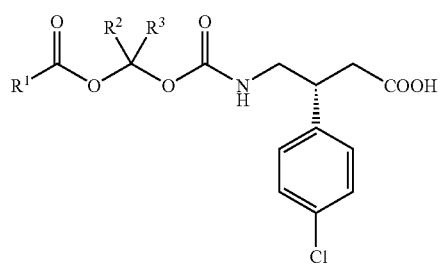

(1)

wherein:
R$^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; and
R$^2$ and R$^3$ are independently chosen from hydrogen, methyl, ethyl, n-propyl, isopropyl, n-butyl, isobutyl, sec-butyl, phenyl, and cyclohexyl.

In certain embodiments of Formula (1), R$^1$ is isopropyl; and one of R$^2$ and R$^3$ is hydrogen and the other of R$^2$ and R$^3$ is isopropyl.

In certain embodiments of Formula (1), the carbon to which R$^2$ and R$^3$ are bonded is of the S-configuration.

In certain embodiments of Formula (1), the carbon to which R$^2$ and R$^3$ are bonded is of the R-configuration.

In certain embodiments of Formula (1), the compound is (3R)-4-{[(1S)-2-methyl-1-(2-methylpropanoyloxy)propoxy]carbonylamino}-3-(4-chlorophenyl)butanoic acid or a salt thereof.

In certain embodiments, methods provided by the present disclosure are used for the preparation of 1-(acyloxy)-alkyl carbamate prodrugs of pregabalin of Formula (2):

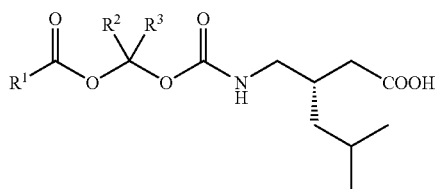

(2)

wherein:
R$^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; and
R$^2$ and R$^3$ are independently chosen from hydrogen, methyl, ethyl, n-propyl, isopropyl, n-butyl, isobutyl, sec-butyl, phenyl and cyclohexyl.

In certain embodiments of Formula (2), each of R$^1$ is isopropyl; one of R$^2$ and R$^3$ is hydrogen; and the other of R$^2$ and R$^3$ is methyl.

In certain embodiments of Formula (2), the carbon to which R$^2$ and R$^3$ are bonded is of the S-configuration.

In certain embodiments of Formula (2), the carbon to which R$^2$ and R$^3$ are bonded is of the R-configuration.

In certain embodiments of Formula (2), the compound is 1-(R)-3-({[1-(2-methylpropanoyloxy)ethoxy] carbonylamino}methyl) (3S)-5-methylhexanoic acid or a salt thereof.

In certain embodiments, methods provided by the present disclosure are used for the preparation of 1-(acyloxy)-alkyl carbamate prodrugs of tranexamic acid of Formula (3):

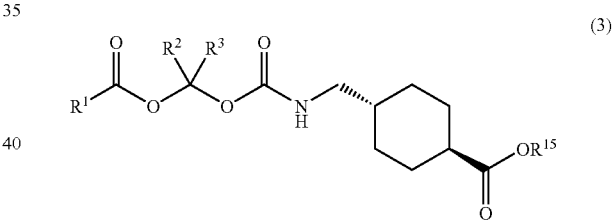

(3)

wherein:
R$^1$ is chosen from $C_{1-4}$ alkyl, phenyl, O-tolyl, and cyclohexyl;
R$^2$ is hydrogen;
R$^3$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; and
R$^{15}$ is chosen from hydrogen, $C_{1-4}$ alkyl, benzyl, 4-methoxybenzyl, diphenylmethyl, triphenylmethyl, trimethylsilyl, triethylsilyl, triisopropylsilyl, tert-butyldimethylsilyl, and phenyldimethylsilyl.

In certain embodiments of Formula (3), R$^1$ is chosen from isopropyl, isobutyl, and phenyl; one of R$^2$ and R$^3$ is hydrogen, and the other of R$^2$ and R$^3$ is chosen from methyl and isopropyl; and R$^{15}$ is hydrogen.

In certain embodiments of Formula (3), R$^1$ is isopropyl; one of R$^2$ and R$^3$ is hydrogen and the other of R$^2$ and R$^3$ is methyl; and R$^{15}$ is hydrogen.

In certain embodiments of Formula (3), the compound is chosen from trans-4-({[(1R/S)-1-(2-methylpropanoyloxy) ethoxy]carbonylamino}methyl)-cyclohexanecarboxylic acid or a salt thereof.

In certain embodiments, methods provided by the present disclosure are used for the preparation of 1-(acyloxy)-alkyl carbamate prodrugs of gabapentin of Formula (4):

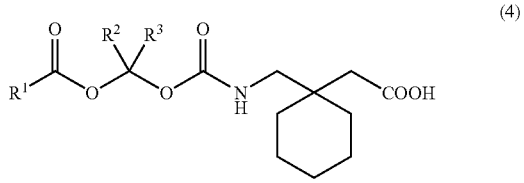

wherein:
$R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; and
$R^2$ and $R^3$ are independently chosen from hydrogen, methyl, ethyl, n-propyl, isopropyl, n-butyl, isobutyl, sec-butyl, phenyl, and cyclohexyl.

In certain embodiments of Formula (4), $R^1$ is isopropyl; one of $R^2$ and $R^3$ is hydrogen; and the other of $R^2$ and $R^3$ is methyl.

In certain embodiments of Formula (4), the carbon to which $R^2$ and $R^3$ are bonded is of the S-configuration.

In certain embodiments of Formula (4), the carbon to which $R^2$ and $R^3$ are bonded is of the R-configuration.

In certain embodiments of Formula (4), the compound is {[(1-isobutanoyloxyethoxy)carbonyl]aminomethyl}-1-cyclohexane acetic acid or a salt thereof.

The step of reacting a compound of Formula (V) or a salt thereof with an N-hydroxysuccinimide compound of Formula (VII) to provide a compound of Formula (I) can be carried out in a suitable solvent such as dichloromethane or acetonitrile, and at an appropriate temperature such as from about room temperature to less than about 40° C. for dichloromethane, and from about room temperature to less than about 81° C. for acetonitrile.

Compounds of Formula (V) or salts thereof may be prepared, for example, using methods disclosed by Raillard et al., U.S. Application No. 61/087,056 filed Aug. 7, 2008.

Methods provided by the present disclosure further provide the step of reacting a compound of Formula (I) or a salt thereof with a primary or secondary amine-containing drug of formula $HNR^9R^{10}$ or a salt thereof to provide a compound of Formula (VI) according to step (ii) as shown in Scheme 1.

Scheme 1

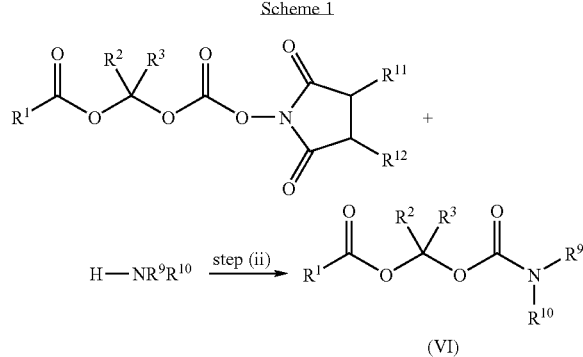

wherein $R^1$, $R^2$, $R^3$, $R^{11}$, and $R^{12}$ are as defined herein, and —$NR^9R^{10}$ is a moiety of a primary or secondary amine-containing drug corresponding to the removal of one hydrogen atom from a single nitrogen atom of a parent primary or secondary amine-containing drug having the structure $HNR^9R^{10}$, wherein $R^9$ is chosen from hydrogen and a bond to $R^{10}$. Methods of synthesizing 1-(acyloxy)-alkyl carbamate prodrugs from 1-(acyloxy)alkyl N-hydroxysuccinimidyl carbonate intermediates are disclosed in Gallop et al., U.S. Pat. Nos. 6,818,787, 6,927,036, 6,972,341, 7,186,855, and 7,227,028; Raillard et al., U.S. Pat. No. 7,232,924; and Gallop and Bhat, WO 2005/010011.

In certain embodiments, step (ii) can be carried out in an appropriate solvent such as, for example, acetone, acetonitrile, dichloromethane, dichloroethane, chloroform, toluene, tetrahydrofuran, dioxane, dimethylformamide, dimethylacetamide, N-methylpyrrolidinone, dimethyl sulfoxide, pyridine, ethyl acetate, methyl tert-butyl ether, methanol, ethanol, isopropanol, tert-butanol, water, or combinations of any of the foregoing. In certain embodiments, the solvent is chosen from acetone, acetonitrile, dichloromethane, toluene, tetrahydrofuran, pyridine, methyl tert-butyl ether, methanol, ethanol, isopropanol, water, and combinations of any of the foregoing. In certain embodiments, the solvent is a mixture of acetonitrile and water. In certain embodiments, the solvent is a mixture of acetonitrile and water, with a volume ratio of acetonitrile to water from about 1:5 to about 5:1. In certain embodiments, the solvent is a mixture of methyl tert-butyl ether and water. In certain embodiments, the solvent is a mixture of methyl tert-butyl ether and water, with a volume ratio of methyl tert-butyl ether to water from about 20:1 to about 2:1. In certain embodiments, the solvent is a mixture of methyl tert-butyl ether and water, wherein the methyl tert-butyl ether contains from about 10% to about 50% acetone by volume. In certain embodiments, the solvent is chosen from dichloromethane, water, and a combination thereof. In certain embodiments, the solvent is a biphasic mixture of dichloromethane and water. In certain embodiments, the solvent is a biphasic mixture of dichloromethane and water containing from about 0.001 equivalents to about 0.1 equivalents of a phase transfer catalyst. In certain embodiments, the phase transfer catalyst is a tetraalkylammonium salt. In certain embodiments, the phase transfer catalyst is a tetrabutylammonium salt.

In certain embodiments, step (ii) can be carried out at a temperature between about −20° C. and about 40° C. In certain embodiments, the temperature of step (ii) is between about −20° C. and about 25° C. In certain embodiments, the temperature of step (ii) is between about 0° C. and about 25° C. In certain embodiments, the temperature of step (ii) is between about 25° C. and about 40° C.

In certain embodiments of step (ii), the reaction can be performed in the absence of a base.

In certain embodiments of step (ii), the reaction can be performed in the presence of an inorganic base. In certain embodiments, the inorganic base is chosen from an alkali metal bicarbonate and an alkali metal carbonate salt. In certain embodiments, the inorganic base is sodium bicarbonate.

In certain embodiments of step (ii), the reaction is performed in the presence of an organic base. In certain embodiments, the organic base is chosen from triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene or 1, and 5-diazabicyclo[4.3.0]undec-7-ene. In certain embodiments, the organic base is chosen from triethylamine, diisopropylethylamine, N-methylmorpholine, and pyridine.

1-(Acyloxy)-alkyl Carbamate Prodrugs

Compounds of the present disclosure include compounds of Formula (VI) or a salt thereof prepared by the methods disclosed herein. Compounds of Formula (VI) prepared according to the disclosed methods may be included in pharmaceutical compositions, which further comprise at least one pharmaceutically acceptable vehicle. Compounds of Formula (VI) or a salt thereof obtained by the methods disclosed herein or a pharmaceutical composition thereof may be used in therapeutic application for treatment of an appropriate disease. For example, compounds of Formula (VI) in which —$NR^9R^{10}$ is a moiety corresponding to the removal of one hydrogen atom from a single nitrogen atom of gabapentin, and pharmaceutical compositions thereof may be used in the treatment of epilepsy, pain such as neuropathic pain or pain associated with irritable bowel syndrome, anxiety such as general anxiety disorder, alcohol dependency such as ethanol withdrawal syndrome, restless legs syndrome, migraine prophylaxis, fibromyalgia, and hot flashes. For example, compounds of Formula (VI) in which —$NR^9R^{10}$ is a moiety corresponding to the removal of one hydrogen atom from a single nitrogen atom of pregabalin and pharmaceutical compositions thereof may be used in the treatment of epilepsy, pain such as neuropathic pain or pain associated with irritable bowel syndrome, anxiety such as general anxiety disorder, alcohol dependency such as ethanol withdrawal syndrome, restless legs syndrome, migraine prophylaxis, fibromyalgia, and hot flashes. Compounds of Formula (VI) in which —$NR^9R^{10}$ is a moiety corresponding to the removal of one hydrogen atom from a single nitrogen atom of R-baclofen and pharmaceutical compositions thereof may be used in the treatment of spasticity, gastro-esophageal reflux disease, emesis, cough, narcotic addiction or abuse, alcohol addiction or abuse, nicotine addiction or abuse, urinary incontinence, neuropathic pain, and musculoskeletal pain such as lower back pain. Compounds of Formula (VI) in which —$NR^9R^{10}$ is a moiety corresponding to the removal of one hydrogen atom from a single nitrogen atom of tranexamic acid and pharmaceutical compositions thereof may be used in the treatment of excessive bleeding such as excessive menstrual bleeding, a skin disease, a skin disorder, and tumor metastasis.

In certain embodiments, —$NR^9R^{10}$ is a moiety of a primary or secondary amine-containing drug corresponding to the removal of one hydrogen atom from a single nitrogen atom of a parent primary or secondary amine-containing drug having the structure $HNR^9R^{10}$, wherein $R^9$ is chosen from hydrogen and a bond to $R^{10}$. In various embodiments, $HNR^9R^{10}$ is chosen from acebutalol, albuterol, alprenolol, atenolol, bunolol, bupropion, butopamine, butoxamine, carbuterol, cartelolol, colterol, deterenol, dexpropanolol, diacetolol, dobutamine, exaprolol, exprenolol, fenoterol, fenyripol, gabapentin, labotolol, levobunolol, metolol, metaproterenol, metoprolol, nadolol, pamatolol, penbutalol, pindolol, pirbuterol, practolol, prenalterol, primidolol, prizidilol, procaterol, propanolol, quinterenol, rimiterol, ritodrine, solotol, soterenol, sulfiniolol, sulfinterol, sulictidil, tazaolol, terbutaline, timolol, tiprenolol, tipridil, tolamolol, thiabendazole, albendazole, albutoin, alendronate, alinidine, alizapride, amiloride, a minorex, aprinocid, cambendazole, cimetidine, cisapride, clonidine, cyclobenzadole, delavirdine, efegatrin, etintidine, fenbendazole, fenmetazole, flubendazole, fludorex, icadronate, lobendazole, mebendazole, metazoline, metoclopramide, methylphenidate, mexiletine, neridronate, nocodazole, oxfendazole, oxibendazole, oxmetidine, pamidronate, parbendazole, pramipexole, prazosin, pregabalin, procainamide, ranitidine, tetrahydrazoline, tiamenidine, tinazoline, tiotidine, tocamide, tolazoline, tramazoline, xylometazoline, dimethoxyphenethylamine, n-[3(R)-[2-piperidin-4-yl)ethyl]-2-piperidone-1-yl]acetyl-3(R)-methyl-β-alanine, adrenolone, aletamine, amidephrine, amphetamine, aspartame, bamethan, betahistine, carbidopa, clorprenaline, chlortermine, dopamine, L-dopa, ephrinephrine, etryptamine, fenfluramine, methyldopamine, norepinephrine, enviroxime, nifedipine, nimodipine, triamterene, pipedemic acid, 1-ethyl-6-fluoro-1,4-dihydro-4-oxo-7-(1-piperazinyl)-1,8-napthyridine-3-carboxylic acid and 1-cyclopropyl-6-fluoro-1,4-dihydro-4-oxo-7-(piperazinyl)-3-quinolinecarboxylic acid, theprubicin, deoxyspergualin, seglitide, nebracetam, benanomicin B, eremomycin, thrazarine, tosufloxacin, baogongteng A, angiopeptin, boholmycin, ravidomycin, tageflar, orienticins, amphotericin B, tiamdipine, doxorubicin, lysobactin, mofegiline, octreotide, oxolide, amikacin, phospholine, nuvanil, cispentacin, chlorotetain, remacemide, ramoplanins, janthinomycins, mersacidin, droxidopa, helvecardin A, helvecardin B, rilmazafone, vigabatrin, amlodipine, (R)-(+)-amlodipine, mideplanin, milnacipran, pranedipine, olradipine, deoxymethylspergualin, fudosteine, trovafloxacin, ceranapril, restricticin, idarubicin, arbekacin, giracodazole, poststatin, pazufloxacin, D-cycloserine, ovothiol A, ceftizoxime, icatibant, p-iodorubidazone, aladapcin, dalargin, seproxetine, pradimicin E, pradimicin FA-2, tafenoquine, sampatrilat, ruboxyl, dactimicin, alatrofloxacin, galarubicin, metaraminol, exatecan, squalamine, paromomycin, leustroducsin A, leustroducsin B, leustroducsin C, lanicemine, azoxybacilin, tetrafibricin, pixantrone, ziconotide, garomefrine, spinorphin, doripenem, alestramustine, seraspenide, safingol, aminolevulinic acid, pelagiomicin C, styloguanidine, L-4-oxalysine, eglumegad, rhodopeptins, mycestericin E, midaxifylline, anisperimus, lagatide, ibutamoren, oritavancin, ecenofloxacin, metyrosine, methyldopa, baclofen, tranylcypromine, micronomicin, zorubicin, epirubicin, gilatide, epithalon, cystamine, pluraflavin A, pluraflavin B, pasireotide, caprazamycin, barusiban, spisulosine, 21-aminoepothilone B, capsavanil, olcegepant, sulphostin, lobophorin A, papuamide A, papuamide B, cystocin, deoxynegamycin, galnon, pyloricidin B, brasilicardin A, neramexane, kaitocephalin, icofungipen, aliskiren, capromorelin, histaprodifen, donitriptan, cambrescidins, tipifarnib, tabimorelin, belactosin A, belactosin C, circinamide, targinine, sulphazocine, nepicastat, oseltamivir, hydrostatin A, butabindide, netamiftide, memantine, fluvoxamine, deferoxamine, tranexamic acid, fortimicin A, cefaclor, lisinopril, ubestatin, cefminox, aspoxicillin, cefcanel, cefcanel daloxate, olamufloxacin, R-(+)-aminoindane, gemifloxacin, kahalalide F, palauamine, examorelin, leustroducsin H, sabarubicin, amifostine, L-homothiocitrulline, L-thiocitrulline, impentamine, neboglamine, amselamine, cetefloxacin, cyclothialidine, fluvirucin B2, loracarbef, cefprozil, sperabillins, milacamide, avizafone, α-methyltryptophan, cytaramycin, lanomycin, decaplanin, eflornithine, L-histidinol, tuftsin, kanamycin, amthamine, sitafloxacin, leurubicin, amantadine, isodoxorubicin, gludopa, bactobolin, esafloxacin, tabilautide, lazabemide, enalkiren, amrubicin, daunorubicin, mureidomycins, pyridazomycin, cimaterol, (+)-isamoltan, N-desmethylmilameline, noberastine, fosopamine, adaprolol, pradimicin B, amosulalol, xamoterol, boholmycin, risotilide, indeloxazine, denopamine, parodilol, utibapril, nardeterol, biemnidin, sparfloxacin, sibanomicin, tianeptine, oberadilol, methoctramine, sezolamide, anabasine, zilpaterol, zabiciprilat, enkastins, ulifloxacin, (+)-sotalol, deoxynojirimycin, altromycin A, altromycin C, dorzolamide, fepradinol, delapril, ciprofloxacin, balofloxacin, mepindolol, berlafenone, ramipril, dopexamine, dilevalol, (−)-nebivolol, duramycin, enalapril, meluadrine, zelandopam, voglibose, sertraline, carvedilol, pafenolol, paroxetine, fluoxetine, phendioxan, salmeterol, solpecainol, repinotan, bambuterol, safinamide, tilisolol, 7-oxostaurosporine, caldaret, sertraline, cilazapril, benazepril, prisotinol, gatifloxacin, ovothiol B, adaprolol, tienoxolol, fluparoxan, alprenoxime, efegatran, pradimicin, salbostatin, ersentilide, (S)-noremopamil, esperamicin A1, batoprazine, ersentilide, osutidine, quinapril, dihydrexidine, argiopine, pradimicin D, frovatriptan, hispidospermidin, silodosin, michellamine B, sibenadet, tetrindol, talibegron, topixantrone, nortopixantrone, tecalcet, buteranol, α-methylepinephrine, nornicotine, thiofedrine, lenapenem, imidapril, epibatidine, premafloxacin, socorromycin, trandolapril, tamsulosin, dirithromycin, inogatran, vicenistatin, immepyr, immepip, balanol, orbifloxacin, maropitant, dabelotine, lerisetron, ertapenem, nolomirole, moxifloxacin, vofopitant, halofuginone, melagatran, ximelagatran, fasudil, isofagomine, pseudoephedrine, propafenone, celiprolol, carteolol, penbutolol, labetalol, acebutolol, reproterol, rimoterol, amoxapine, maprotiline, viloxazine, protriptyline, nortriptyline, desipramine, oxprenolol, propranolol, ketamine, butofilolol, flecamide, tulobuterol, befunolol, immucillin-H, vestipitant, cinacalcet, lapatinib, desloratadine, ladostigil, vildagliptin, tulathromycin B, becampanel, salbutamol, delucemine, solabegron, paroxetine, gaboxadol, telavancin, ralfinamide, tomoxetine, dalbavancin, elarofiban, ferulinolol, fenoldopam, sumanirole, sarizotan, brinzolamide, pradofloxacin, garenoxacin, reboxetine, ezlopitant, palindore, nebivolol, dinapsoline, proxodolol, repinotan, demexiptiline, mitoxantrone, norfloxacin, dilevalol, nipradilol, esmolol, ibopamine, troxipide, arotinolol, formoterol, bopindolol, cloranolol, mefloquine, perindopril, mabuterol, bisoprolol, bevantolol, betaxolol, tertatolol, enoxacin, lotrafiban, moexipril, droxinavir, adrogolide, alniditan, tigecycline, lubazodone, meropenem, temocapril, napsamycins, (−)-cicloprolol, ecteinascidins, alprafenone, landiolol, tirofiban, noberastine, rasagiline, setazindol, picumeterol, arbutamine, mecamylamine, delfaprazine, imidapril, midafotel, manzamines, binospirone, duloxetine, and litoxetine. Other secondary or primary amine drugs $HNR^9R^{10}$ are described in various compendia accessible to the skilled artisan, such as, for example, the Merck Index, $13^{th}$ Edition, 2001 or the Physicians Desk Reference, $59^{th}$ Edition, 2005. Accordingly, secondary or primary amine-containing drugs $HNR^9R^{10}$ described in such references are encompassed by the present disclosure. The corresponding 1-(acyloxy)-alkyl carbamate prodrug synthesized according to the methods provided by the present disclosure and pharmaceutical compositions thereof may be used to treat a disease for which the parent secondary or primary amine-containing drug is therapeutically effective.

In certain embodiments, $HNR^9R^{10}$ is chosen from alendronate, amifostine, rac-baclofen, R-baclofen, carbidopa, clonidine, ciprofloxacin, cisapride, daunorubicin, doxorubicin, fenoldopam, fenoterol, gabapentin, gentamycin, kanamycin, levodopa, meropenem, metazoline, neomycin, pamidronate, pregabalin, tobramycin, trovafloxacin, and vigabatrin. In certain embodiments, $HNR^9R^{10}$ is chosen from gabapentin, pregabalin, R-baclofen, and tranexamic acid. In certain embodiments, $HNR^9R^{10}$ is a GABA analog as defined herein.

EXAMPLES

The following examples describe in detail the methods provided by the present disclosure. It will be apparent to those skilled in the art that many modifications, both to materials and methods, may be practiced without departing from the scope of the disclosure.

Description 1

1-Chloroethyl (4-methylthiophenoxy)formate (D1)

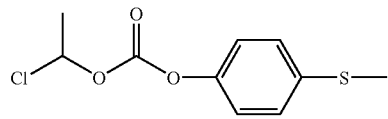

Method A 4-(Methylthio)phenol (15.0 g) and dichloromethane (100 mL) were charged to a vessel. The vessel was cooled to ca. 0° C. 1-Chloroethyl chloridocarbonate (14 mL) was added. Triethylamine was then slowly added using an addition funnel while maintaining the temperature below 15° C. The reaction mixture was then stirred at ca. 0° C. for 10 minutes and then stirred overnight at room temperature. The reaction mixture was then washed with water (2×50 mL) followed by evaporation to an oil. The residue was cooled in a freezer overnight (−10° C.) and then washed with heptane (18 mL) and tert-butyl methyl ether (10 mL) to provide 23.75 g of the title compound (D1).

Method B 4-(Methylthio)phenol (220.0 g) and dichloromethane (1.1 L) were charged to a vessel. 1-Chloroethyl chloroformate (235.5 g) was added. The vessel was cooled to −5° C. Triethylamine (167.0 g) was slowly added using an addition funnel while maintaining the temperature below 10° C. Following the addition of triethylamine, the reaction mixture was warmed to 20-25° C. and stirred for ca. 2 hours. Water (650 mL) was added to the reaction, stirred for 15 minutes, and then settled for 15 minutes. The light yellow aqueous layer was removed and discarded. The organic layer was washed twice with water (600 mL). The dichloromethane was distilled under reduced pressure to provide 382 g of crude product as an oil. Heptane (700 mL) was added to the crude product and the mixture heated to 60° C. to give a brown solution. The solution was slowly cooled to 8° C. Heptane (200 mL) and tert-butyl methyl ether (50 mL) were added and the solution further cooled to 0° C. The mixture was stirred at 0° C. for 2 hours to give a slurry, which was filtered and the filtrate washed with heptane (120 mL). The product was dried overnight under vacuum at 25° C. The weight of the dry product was 312.2 g. A second crop of product (60.6 g) was obtained from the mother liquor after the solvents were stripped off to provide an overall yield of the title compound (D1) of 96%.

Method C 4-(Methylthio)phenol (28 g) and dichloromethane (100 mL) were charged to a vessel. The vessel was cooled to approximately 0° C. 1-Chloroethyl chloroformate (14 mL) was added. A solution of 4-methylmorpholine (24 g) in dichloromethane (100 mL) was slowly added using an addition funnel, keeping the temperature below 15° C. The reaction mixture was then stirred at approximately 0° C. for 10 minutes and then stirred at room temperature overnight. The reaction mixture was then washed with water (2×200 mL) followed by evaporation to provide 48 g of the title compound (D1) as an oil.

Description 2

(4-Methylthiophenoxycarbonyloxy)ethyl 2-methylpropanoate (D2)

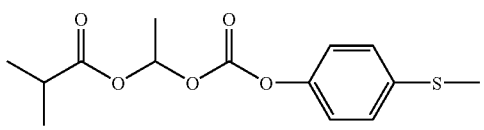

Method A

Chloroethyl(4-methylthiophenoxy)formate D1 (18.4 g, may be prepared as in Description 1) and 2-methylpropanoic acid (20 mL) was charged to a vessel. Silver isobutyrate (15.3 g) was added and the vessel was rinsed with 2-methylpropanoic acid (15 mL). The reaction was heated to 95° C. and the mixture was maintained at approximately 90° C. for 1 hour. The reaction was then cooled to room temperature and tert-butyl methyl ether (120 mL) was added. The solid was filtered and the filtrate washed with tert-butyl methyl ether (2×50 mL). Water (60 mL) and brine (50 mL) were added to the residue and stirred for approximately 10 minutes. The tert-butyl methyl ether layer was washed with water (2×80 mL). This was then evaporated to form an oil.

Tert-butyl methyl ether (200 mL), water (150 mL), and a saturated solution of sodium hydrogen carbonate (100 mL) was added to the oil and the mixture was stirred for 15 minutes. The aqueous layer was separated. The residue was evaporated and vacuum distilled at approximately 10 mm Hg at 80-90° C. to provide 22.0 g of the title compound D2.

Method B 4-(Methylthio)phenol (47.2 g) and dichloromethane (236 mL) were charged to a vessel. 1-Chloroethyl chloroformate (50.5 g) was added. The vessel was cooled to approximately 0° C. Triethylamine (35.7 g) was slowly added to the reaction vessel using an addition funnel while maintaining the temperature below 20° C. When the addition of triethylamine was completed, the reaction mixture was warmed to 20° C. and stirred for approximately 1 hour. The reaction mixture was washed with water (141 mL) twice. Dichloromethane was distilled under reduced pressure to give an oily residue. Dimethyl carbonate (47 mL) was added to the residue. The reaction was stirred to a solution. The crude product was used directly in the next step.

To the crude product in dimethyl carbonate solution was charged isobutyric acid (94 mL) and copper (I) oxide (48.1 g). The reaction was heated to ca. 100° C. and stirred for 6 hours. The progress of the reaction was monitored by HPLC. The mixture was cooled to ca. 0° C. and heptane (400 mL) added. Ten percent (10%) ammonium hydroxide (500 mL) was slowly added to maintain the temperature below 20° C. The mixture was stirred at 10-20° C. for 1 hour. The solid was then filtered out. The aqueous layer was removed from the vessel and the organic layer was washed twice with 10% ammonium hydroxide (400 mL) and once with water (300 mL). The solvents were distilled under reduced pressure to provide 99.5 g (79.3% yield) of the title compound D2 as an oil.

Method C

1-Chloroethyl (4-methylthiophenoxy)formate D1 (20.0 g, may be prepared as in Description 1), sodium iodide (12.1 g), dimethyl carbonate (20 mL), and isobutyric acid (60 mL) were added to a reaction vessel under nitrogen. N,N-diisopropylethylamine (21.2 g) was slowly added with cooling. The reaction mixture was heated to 80° C. and stirred for ca. 3 hours. Heptane (160 mL) was added to the reaction. After cooling in ice bath, 10% ammonium hydroxide (100 mL) was slowly added to the reaction. The aqueous layer was removed and the organic layer was washed twice with 10% ammonium hydroxide. The solvents were distilled under vacuum to provide 20.8 g (86% yield) of the title compound D2.

Method D

2-Methylpropanoic acid (5 mL) and silver (I) oxide (2.3 g) were charged to a vessel at room temperature. Chloroethyl (4-methylthiophenoxy)formate D1 (2.46 g) was added to the reaction vessel. The reaction mixture was heated to 95° C. and the temperature was maintained at approximately 90° C. for one hour. The reaction was then cooled to room temperature and tert-butyl methyl ether (20 mL) was added. Solid material was filtered off and the rinsed with tert-butyl methyl ether (2×15 mL). The organic phase was washed with water (4×25 mL), bicarbonate (2×25 mL), and dried over sodium sulfate. The organic volatiles were removed under vacuum to provide 2.9 g of the title compound D2 as a pale yellow-oil.

Description 3

[4-(Methylsulfonyl)phenoxycarbonyloxy]ethyl 2-methylpropanoate (D3)

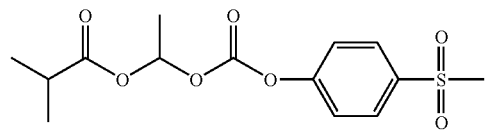

Method A

Dichloromethane (100 mL) and (4-methylthiophenoxycarbonyloxy)ethyl 2-methylpropanoate D2 (20.1 g; may be prepared as in Description 2) were charged to a vessel at 0° C. Peracetic acid (32 mL; 32 wt % in acetic acid) was slowly added using an addition funnel over approximately 25 minutes. The reaction was then stirred at 0-5° C. for 2 hours. Water (70 mL) was added and the reaction was stirred for 10 minutes and then settled for 10 minutes. The organic layer was washed with water (2×70 mL). The solvents were then evaporated to provide an oil, which was stored overnight at −5° C. The residue was dried using a vacuum pump (ca. 10 mm Hg) for 6 hours to provide 21.4 g of the title compound (D3).

Method B (4-Methylthiophenoxycarbonyloxy)ethyl 2-methylpropanoate D2 (20.5 g, may be prepared as in Description 2), acetone (160 mL), and water (40 mL) were charged to reaction vessel at ca. 21° C. Oxone® solid (61.5 g) was slowly added over ca. 10 minutes while maintaining the temperature about 21-35° C. The reaction was cooled as necessary. The reaction was then stirred for 2 hours at 20-25° C. The reaction mixture was filtered and the filtrate washed twice with tert-butyl methyl ether (30 mL). The solvents were distilled under reduced pressure to provide ca. 50 mL. Tert-butyl methyl ether (80 mL) and water (15 mL) were added to the reaction. The product was extracted into a tert-butyl methyl ether solution. The tert-butyl methyl ether was then distilled under reduced pressure. n-Propanol (60 mL) was added to the reaction and distilled under reduced pressure. n-Propanol (67 mL) and water (67 mL) were added to the mixture. The mixture was then stirred at room temperature to provide a clear solution. Water (67 mL) was slowly added to the vessel at 30-35° C. using an addition funnel. The mixture was stirred overnight and then cooled in an ice-bath. After stirring for 3 hours, the product was filtered out, rinsed with water (40 mL) and heptane (20 mL). The product was then dried to provide 17.71 g (80.1% yield) of the title compound D3.

Method C

Dichloromethane (50 mL) and (4-methylthiophenoxycarbonyloxy)ethyl 2-methylpropanoate D2 (2.9 g) were charged to a vessel at 0° C. Peracetic acid (6.8 mL; 32 wt % in acetic acid) was slowly added using an addition funnel over approximately 25 minutes. The reaction was then stirred at 0-5° C. for 2 hours. Water (50 mL) was added and the reaction mixture was stirred for 10 minutes and then allowed to settle for 10 minutes. The organic layer was separated and washed with water (2×50 mL). The solvents were then evaporated to provide 3 g of the title compound D3 as an oil.

Description 4

1-Chloro-2-methylpropyl (4-methylthiophenoxy)formate (D4)

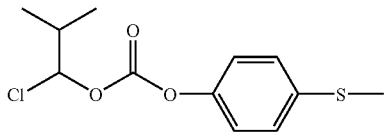

4-(Methylthio)phenol (28 g) and dichloromethane (100 mL) were charged to a vessel. The vessel was cooled to approximately 0° C. 1-Chloro-2-methylpropyl chloroformate (14 mL) was added. A solution of 4-methylmorpholine (24 g) in dichloromethane (100 mL) was then slowed added using an addition funnel, keeping the temperature below 15° C. The reaction mixture was then stirred at approximately 0° C. for 10 minutes. The reaction mixture was then stirred at room temperature overnight. The reaction mixture was washed with water (2×100 mL) followed by evaporation to an oil. Fifty-four grams (54 g) of the title compound D4 was obtained.

Description 5

2-Methyl-1-(4-methylthiophenoxycarbonyloxy)propyl 2-methylpropanoate (D5)

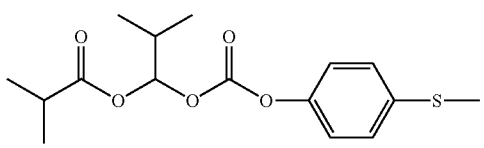

2-Methylpropanoic acid (5 mL) and silver (I) oxide (2.3 g) were charged to a vessel at room temperature. 1-Chloro-2-methylpropyl (4-methylthiophenoxy)formate (2.46 g) D4 was added to the reaction vessel. The reaction was heated to 95° C. and the mixture was maintained at approximately 90° C. for 1 hour. The reaction was then cooled to room temperature and tert-butyl methyl ether (20 mL) was added. The solid was filtered and the filter was washed with tert-butyl methyl ether (2×15 mL). The organic phase was washed with water (4×25 mL), bicarbonate (2×25 mL), and dried over sodium sulfate. The organic volatiles were removed under vacuum to provide 3.2 g of the title compound D5 as a pale-yellow oil.

Description 6

2-Methyl-1-[4-(methylsulfonyl)phenoxycarbonyloxy]propyl 2-methylpropanoate (D6)

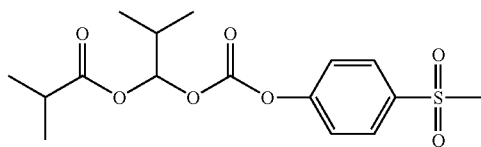

Dichloromethane (50 mL) and 2-methyl-1-(4-methylthiophenoxycarbonyloxy)propyl 2-methylpropanoate D5 (2.9 g) were charged to a vessel at 0° C. Peracetic acid (6.8 mL; 32 wt % in acetic acid) was slowly added using an addition funnel over approximately 25 minutes. The reaction was then stirred at 0-5° C. for 2 hours. Water (50 mL) was added and the reaction was stirred for 10 minutes and then allowed to settle for 10 minutes. The organic layer was washed with water (2×50 mL). The solvents were then evaporated to provide 3.5 g of the title compound D6 as an oil.

Example 1

(2,5-Dioxoazolidinyloxycarbonyloxycarbonyloxy)ethyl 2 2-methylpropanoate (E1)

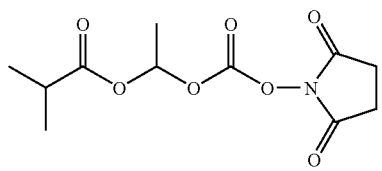

[4-(Methylsulfonyl)phenoxycarbonyloxy]ethyl 2-methylpropanoate D3 is dissolved in dichloromethane at a concentration of 10% (w/vol). N-hydroxysuccinimide (1.1 equivalents) is added to the solution. The reaction mixture is warmed to reflux and stirred until the reaction is complete. The organic phase is extracted twice with a 10% potassium carbonate solution followed by a wash with water (2×). Drying over sodium sulfate is followed by solvent evaporation to provide the title compound E1.

Example 2

1-(2,5-Dioxoazolidinyloxycarbonyloxy)-2-methylpropyl 2-methylpropanoate (E2)

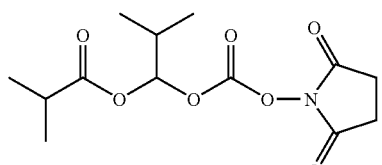

2-Methyl-1-[4-(methylsulfonyl)phenoxycarbonyloxy] propyl 2-methylpropanoate D6 is dissolved in dichloromethane at a concentration of 10% (w/vol). N-hydroxysuccinimide (1.1 equivalents) is added to the solution. The reaction mixture is warmed to reflux and stirred until the reaction is complete. The organic phase is extracted twice with a 10% potassium carbonate solution followed by a wash with water (2×). Drying over sodium sulfate is followed by solvent evaporation to provide the title compound E2.

Example 3

[4-(Methylsulfonyl)phenoxycarbonyloxy]ethyl 2-methylpropanoate (D3)

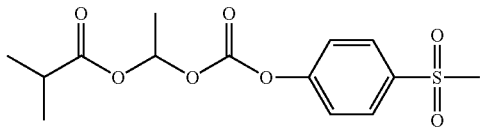

Step A: 1-Chloroethyl-(4-methylthiophenoxy)formate (D1)

A 250-mL, three-neck, round-bottomed flask equipped with a mechanical stirrer, a 50-mL pressure-equalizing addition funnel, an internal thermometer, and a nitrogen inlet was charged with chloroethyl chloroformate (10.8 g, 76 mmol) and 4-(methylthio)phenol (10 g, 71 mmol) in dichloromethane (75 mL). The resulting clear reaction mixture was cooled to 0° C. A solution pyridine (6.8 g, 86 mmol) in dichloromethane (10 mL) was slowly added over a period of 30 minutes. The reaction mixture was then stirred overnight at room temperature. The reaction mixture was poured into a separatory funnel, washed with water (100 mL), brine (100 mL), dried over sodium sulfate, and evaporated under vacuum to give the title compound D1 as a viscous oil (~17 g, quantitative yield). $^1$H NMR (CDCl$_3$, 400 MHz): δ 1.89 (d, J=6 Hz, 3H), 2.47 (s, 3H), 6.46 (q, J=6 Hz, 1H), 7.11 (d, J=8.4 Hz, 2H), 7.24 (d, J=8.8 Hz, 2H).

Step B: Iodoethyl (4-methylthiophenoxy)formate (E3b)

A 50 mL, three-neck, round-bottomed flask equipped with a magnetic stir bar, a reflux condenser, an internal thermometer, and a nitrogen inlet was charged with chloro-ester D1 (2 g, 8 mmol) and sodium iodide (1.8 g, 12 mmol) in acetonitrile (10 mL). The resulting slurry was warmed to 50° C. for 36 hours. The reaction mixture was cooled to room temperature and inorganic solids were removed by filtration. The clear organic phase was concentrated to give a viscous-oil. The crude product was purified by column chromatography using ethyl acetate and hexane to give the title compound E3b as a viscous-oil (1 g, ~30% yield). $^1$H NMR (CDCl$_3$, 400 MHz): δ 2.31 (d, J=5.6 Hz, 3H), 2.47 (s, 3H), 6.80 (q, J=6 Hz, 1H), 7.11 (d, J=8.4 Hz, 2H), 7.24 (d, J=8.8 Hz, 2H).

Step C: (4-Methylthiophenoxycarbonyloxy)ethyl 2-methylpropanoate (D2)

A 50 mL, three-neck, round-bottomed flask equipped with a magnetic stir bar, an internal thermometer, and a nitrogen inlet was charged with isobutyric acid (10 mL) and 4-methylmorpholine (5 mL). The reaction mixture was stirred at room temperature for 10 minutes and iodo-carbonate E3b (3.1 g, 2.9 mmol) was added. The resulting clear reaction mixture was stirred overnight at 50° C. The reaction mixture was cooled to room temperature and diluted with diethyl ether (20 mL). The organic phase was washed with saturated aqueous sodium bicarbonate (3×10 mL) and concentrated under vacuum to give a viscous oil. The crude product was purified by column chromatography using ethyl acetate and hexane to provide the title compound D2 as a viscous oil (600 mg, 68% yield). $^1$H NMR (CDCl$_3$, 400 MHz): δ 1.18 (d, J=6.8 Hz, 6H), 1.59 (d, J=5.6 Hz, 3H), 2.46 (s, 3H), 2.59 (m, 1H), 6.79 (q, J=5.6 Hz, 1H), 7.11 (d, J=8.8 Hz, 2H), 7.25 (d, J=8 Hz, 2H).

Step D: [4-(Methylsulfonyl)phenoxycarbonyloxy]ethyl 2-methylpropanoate (D3)

A 50 mL, single-neck, round-bottomed flask equipped with a magnetic stir bar, and a nitrogen inlet was charged with sulfide D2 (600 mg, 2 mmol) in methanol (2 mL) and water (2 mL). The resulting clear reaction mixture was cooled to 0° C. and potassium peroxymonosulfate (oxone, 3 g, 4.8 mmol) was slowly added over a period of 10 minutes. The reaction mixture was then stirred for six hours at room temperature. The reaction mixture was then diluted diethyl ether (20 mL) and the organic phase washed with water (10 mL) and 5% aqueous sodium thiosulfate (10 mL). The organic phase was dried and evaporated under vacuum to give a viscous oil. The crude product was purified by column chromatography using ethyl acetate and hexane to give the title compound D3 as a viscous oil (500 mg, 75% yield). $^1$H NMR (CDCl$_3$, 400 MHz): δ 1.20 (d, J=7.2 Hz, 6H), 1.61 (d, J=5.6 Hz, 3H), 2.59 (m, 1H), 3.05 (s, 3H), 6.81 (q, J=5.6 Hz, 1H), 7.40 (d, J=8.8 Hz, 2H), 7.96 (d, J=8.8 Hz, 2H).

All of the patents, publications, applications and other references cited herein are incorporated herein by reference in their entirety.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A method of synthesizing a 1-(acyloxy)alkyl N-hydroxysuccinimidyl carbonate compound of Formula (I) or a salt thereof comprising:
reacting a compound of Formula (V) or a salt thereof with an N-hydroxysuccinimidyl compound of Formula (VII) or a salt thereof to provide the corresponding compound of Formula (I) or a salt thereof:

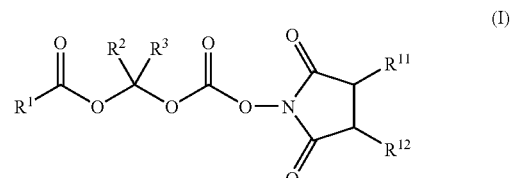

(I)

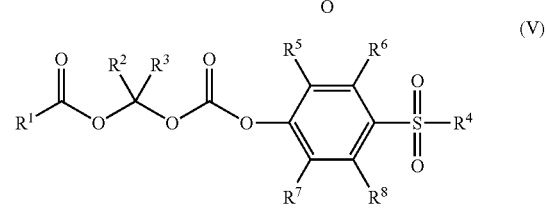

(V)

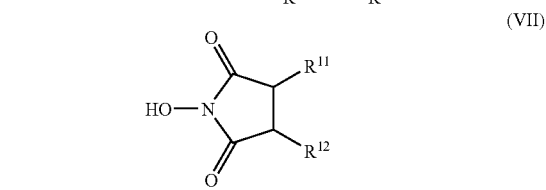

(VII)

wherein:
$R^1$ is chosen from $C_{1-6}$ alkyl, substituted $C_{1-6}$ alkyl, $C_{3-6}$ cycloalkyl, substituted $C_{3-6}$ cycloalkyl, phenyl, substituted phenyl, and $C_{7-9}$ phenylalkyl;

$R^2$ and $R^3$ are independently chosen from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, and $C_{7-9}$ phenylalkyl; or $R^2$ and $R^3$ together with the carbon atom to which they are bonded form a ring chosen from a cyclobutyl, cyclopentyl, and cyclohexyl ring;

$R^4$ is chosen from $C_{1-4}$ alkyl and substituted $C_{1-4}$ alkyl wherein each of the one or more substituent groups is independently chosen from halogen, halo-$C_{1-3}$ alkyl, hydroxyl, and cyano;

each of $R^5$, $R^6$, $R^7$, and $R^8$ is independently chosen from hydrogen, halogen, $C_{1-3}$ alkyl, and halo-$C_{1-3}$ alkyl; and $R^{11}$ and $R^{12}$ are independently chosen from hydrogen, $C_{1-16}$ acylamino, $C_{1-16}$ acyloxy, $C_{1-6}$ alkoxycarbonylamino, $C_{1-6}$ alkoxycarbonyloxy, $C_{1-4}$ alkyl, substituted $C_{1-4}$ alkyl, $C_{1-6}$ alkoxy, substituted $C_{1-6}$ alkoxy, $C_{6-12}$ aryl, substituted $C_{6-12}$ aryl, $C_{7-16}$ arylalkyl, $C_{1-6}$ carbamoyl, $C_{1-6}$ dialkylamino, $C_{5-12}$ heteroaryl, hydroxyl, and sulfonamide; or $R^{11}$ and $R^{12}$ together with the atoms to which they are bonded form a ring chosen from a substituted $C_{3-12}$ cycloalkyl, substituted $C_{3-12}$ heterocycloalkyl, and substituted $C_{6-12}$ aryl ring.

2. The method of claim 1, wherein the method comprises: reacting the compound of Formula (I) or a salt thereof with a primary or secondary amine-containing drug of the formula $HNR^9R^{10}$ or a salt thereof to provide a corresponding 1-(acyloxy)-alkyl carbamate compound of Formula (VI):

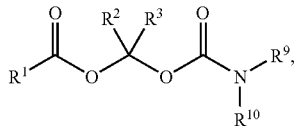

(VI)

wherein —$NR^9R^{10}$ is a moiety of a primary or secondary amine-containing drug.

3. The method of claim 1, wherein $R^1$ is chosen from methyl, ethyl, n-propyl, isopropyl n-butyl, isobutyl, sec-butyl, tert-butyl, n-pentyl, isopentyl, sec-pentyl, neopentyl, 1,1,diethoxyethyl, phenyl, and cyclohexyl.

4. The method of claim 1, wherein one of $R^2$ and $R^3$ is hydrogen; and the other of $R^2$ and $R^3$ is chosen from hydrogen, methyl, ethyl, n-propyl, isopropyl, n-butyl, isobutyl, sec-butyl, phenyl, and cyclohexyl.

5. The method of claim 1, wherein $R^1$ is isopropyl; $R^2$ is methyl; and $R^3$ is hydrogen.

6. The method of claim 1, wherein $R^1$ is isopropyl; $R^2$ is isopropyl; and $R^3$ is hydrogen.

7. The method of claim 1, wherein $R^4$ is chosen from $C_{1-4}$ alkyl, phenyl, and $C_{5-6}$ cycloalkyl.

8. The method of claim 1, wherein $R^4$ is $C_{1-4}$ alkyl.

9. The method of claim 1, wherein $R^4$ is methyl.

10. The method of claim 1, wherein each of $R^5$, $R^6$, $R^7$, and $R^8$ is hydrogen.

11. The method of claim 1, wherein each of $R^{11}$ and $R^{12}$ is hydrogen.

12. The method of claim 1, wherein $R^{11}$ and $R^{12}$ are independently chosen from acetoxy, isobutyroyloxy, pivaloyloxy, benzoyloxy, $C_{1-4}$ alkyl-substituted benzoyloxy, methoxy, and benzyloxy.

13. The method of claim 12, wherein $R^{11}$ and $R^{12}$ are the same and are chosen from isobutyroyloxy and benzoyloxy.

14. The method of claim 1, wherein one of $R^2$ and $R^3$ is hydrogen; and the other of $R^2$ and $R^3$ is chosen from hydrogen, methyl, ethyl, n-propyl, isopropyl, n-butyl, isobutyl, sec-butyl, phenyl, and cyclohexyl; $R^4$ is chosen from $C_{1-4}$ alkyl, phenyl, and $C_{5-6}$ cycloalkyl; each of $R^5$, $R^6$, $R^7$, and $R^8$ is hydrogen; and $R^{11}$ and $R^{12}$ are the same and are chosen from hydrogen, isobutyroyloxy, and benzoyloxy.

15. The method of claim 2, wherein $HNR^9R^{10}$ is chosen from gabapentin, pregabalin, R-baclofen, and tranexamic acid.

16. The method of claim 15, wherein the compound of Formula (VI) is {[(1-isobutanoyloxyethoxy)carbonyl]aminomethyl}-1-cyclohexane acetic acid or a salt thereof.

17. The method of claim 15, wherein the compound of Formula (VI) is (3R)-4-{[(1S)-2-methyl-1-(2-methylpropanoyloxy)propoxy]carbonylamino}-3-(4-chlorophenyl)butanoic acid or a salt thereof.

18. The method of claim 15, wherein the compound of Formula (VI) is 1-(R)-3-({[1-(2-methylpropanoyloxy)ethoxy]carbonylamino}methyl) (3S)-5-methylhexanoic acid or a salt thereof.

19. The method of claim 15, wherein the compound of Formula (VI) is trans-4-({[(1R/S)-1-(2-methylpropanoyloxy)ethoxy]carbonylamino}methyl)-cyclohexanecarboxylic acid or a salt thereof.

* * * * *